(12) United States Patent
Redmond et al.

(10) Patent No.: US 8,632,798 B2
(45) Date of Patent: Jan. 21, 2014

(54) CEREAL β GLUCAN COMPOSITIONS, METHODS OF PREPARATION AND USES THEREOF

(75) Inventors: Mark J. Redmond, Edmonton (CA); David A. Fielder, Edmonton (CA)

(73) Assignee: Ceapro Inc., Edmonton, Alberta (CA)

( * ) Notice: Subject to any disclaimer, the term of this patent is extended or adjusted under 35 U.S.C. 154(b) by 130 days.

(21) Appl. No.: 12/716,588

(22) Filed: Mar. 3, 2010

(65) Prior Publication Data

US 2010/0158988 A1 Jun. 24, 2010

Related U.S. Application Data

(62) Division of application No. 10/498,568, filed as application No. PCT/CA02/01896 on Dec. 11, 2002, now abandoned.

(60) Provisional application No. 60/338,649, filed on Dec. 11, 2001.

(51) Int. Cl.
*A61F 13/00* (2006.01)

(52) U.S. Cl.
USPC ............ 424/443; 424/422; 606/139; 606/228

(58) Field of Classification Search
None
See application file for complete search history.

(56) References Cited

U.S. PATENT DOCUMENTS

| | | | |
|---|---|---|---|
| 4,024,871 A * | 5/1977 | Stephenson | 606/231 |
| 4,028,468 A | 6/1977 | Hohner et al. | |
| 4,471,871 A | 9/1984 | Rockliffe et al. | |
| 4,562,020 A | 12/1985 | Hijiya et al. | |
| 4,774,093 A | 9/1988 | Provonchee et al. | |
| 5,013,561 A | 5/1991 | Goering et al. | |
| 5,332,594 A | 7/1994 | Heller | |
| 5,512,287 A | 4/1996 | Wang et al. | |
| 5,607,677 A | 3/1997 | Jamas et al. | |
| 5,614,242 A | 3/1997 | Fox | |
| 5,676,967 A | 10/1997 | Williams et al. | |
| 5,686,123 A | 11/1997 | Lindahl et al. | |
| 5,741,495 A | 4/1998 | Jamas et al. | |
| 5,827,937 A | 10/1998 | Agerup | |
| 5,980,918 A | 11/1999 | Klein | |
| 6,017,550 A | 1/2000 | Berk et al. | |
| 6,020,016 A | 2/2000 | Castleberry | |
| 6,149,941 A | 11/2000 | Schwarz et al. | |
| 6,168,799 B1 | 1/2001 | Klein | |
| 6,284,886 B1 | 9/2001 | Redmond | |
| 6,323,338 B1 | 11/2001 | Potter et al. | |
| 6,426,201 B1 | 7/2002 | Morgan | |
| 6,800,329 B2 | 10/2004 | Horstmann et al. | |
| 2002/0018807 A1 | 2/2002 | Schmitz et al. | |
| 2002/0054917 A1 | 5/2002 | Gohlke | |
| 2002/0055697 A1* | 5/2002 | Klein | 602/41 |
| 2002/0119928 A1 | 8/2002 | McAnalley | |
| 2004/0005364 A1 | 1/2004 | Klein et al. | |

FOREIGN PATENT DOCUMENTS

| | | |
|---|---|---|
| CA | 1191083 A | 7/1985 |
| CA | 2361308 | 8/2000 |
| EP | 0 328 317 | 8/1989 |
| FR | 2 537 496 | 6/1984 |
| JP | 10-095708 A | 4/1996 |
| JP | 8-169817 A | 7/1996 |
| JP | 08169817 | 7/1996 |
| JP | 10-095708 | 4/1998 |
| JP | 2001-253826 A | 9/2001 |
| JP | 2001-258502 A | 9/2001 |
| WO | 97/41835 A1 | 11/1997 |
| WO | 98/13056 A | 4/1998 |
| WO | 98/39980 A1 | 9/1998 |
| WO | 00/12024 A1 | 3/2000 |
| WO | 00/18365 A | 4/2000 |
| WO | 00/47190 A2 | 8/2000 |
| WO | WO 00/49052 | 8/2000 |
| WO | 00/56268 A | 9/2000 |
| WO | WO 00/56268 A2 | 9/2000 |
| WO | 00/67626 A2 | 11/2000 |
| WO | 01/30403 A1 | 5/2001 |
| WO | 01/57092 A | 8/2001 |
| WO | WO 01/57092 A1 | 8/2001 |
| WO | 01/70194 A1 | 9/2001 |
| WO | WO 02/072687 A2 | 9/2002 |
| WO | WO 02/076358 A1 | 10/2002 |

OTHER PUBLICATIONS

Wikipedia. org., (Saponin).
Collins (J. Agric. Food Chem. 1989, 37 pp. 60-66).
S. Tejinder, "Preparation and Characterization of Films Using Barley and Oat β-lucan Extracts," Cereal Chemistry, vol. 80, No. 6, 2003, pp. 728-731.
Emmons et al., "Antioxidant Activity and Phenotic Contents or Oat Groats and Hulls," Cereal Chemistry, vol. 76, pp. 902-906.
http://en.wikipedia.org/wiki/Avenanthramide.
Kato, T. et al., Spine (Breeding Science), 1995, pp. 471-477, untranslated, Summary in English begins on p. 476.
Japanese Office Action mailed Sep. 9, 2010, Patent Application No. 2003-554788, 4 pages.

* cited by examiner

*Primary Examiner* — James Rogers
(74) *Attorney, Agent, or Firm* — Rothwell, Figg, Ernst & Manbeck P.C.

(57) ABSTRACT

Cereal β(1-3) β(1-4) glucan is used as a film or coating agent to produce clear, edible, biodegradable, delivery, lubricating, and protecting agents. Cereal β(1-3) β(1-4) glucans are distinctive polymers of glucose differentiated from other polymers by not only their source but also their physicochemical properties. The β(1-3) β(1-4) forms a matrix to sequester other materials, such as pharmaceutical, medical and therapeutic agents, flavors, fragrances. The technology has applications to essential oils and non-aqueous materials that are rendered deliverable by the β(1-3) β(1-4) glucan. The β(1-3) β(1-4) glucan films described may be consumed whereby they dissolve in the mouth in a controlled manner and may be used for the delivery of pharmaceutical, medical or confectionery products.

3 Claims, 1 Drawing Sheet

CEREAL β GLUCAN COMPOSITIONS, METHODS OF PREPARATION AND USES THEREOF

CROSS-REFERENCE TO RELATED APPLICATIONS

The present application is a division of U.S. patent application Ser. No. 10/498,568 filed on 21 Jul. 2004, which in turn is a national stage filing under 35 U.S.C. §371 of PCT/CA02/01896, filed on 11 Dec. 2002, which claims benefit under 35 U.S.C. §119(e) to U.S. provisional patent application No. 60/338,649, filed 11 Dec. 2001.

TECHNICAL FIELD

The present invention relates generally to cereal β(1-3) β(1-4) glucans. More particularly, the invention relates to methods for producing thin-films and coatings prepared from oat β(1-3) β(1-4) glucans. The present invention also relates to compositions containing cereal β(1-3) β(1-4) glucans together with other compounds such as pharmaceutical, medical and therapeutic agents; flavours; or fragrances to name only a few.

Also included are novel application methods of thin films and coatings which may be sprayed, dusted, or dip-coated onto products. Of significance are enteric coatings, protective coatings against breakage or environmental hazard exposure. This technology has the added benefit of binding materials at lower temperatures and has particular application to materials that are irregularly shaped and otherwise difficult to wrap.

BACKGROUND OF THE INVENTION

Gums are either hydrophobic or hydrophilic substances of molecular weight ranging from 10,000 to 50,000,000 Daltons, that in an appropriate solvent produce gels or highly viscous suspensions or solutions at low dry substance content. Gums commonly used in food, medicine, and industrial products include starches, cellulose derivatives, pullulan, agar, aloe, gellan, guar gum, locust bean gum, pectin, algin, carrageenan, xanthan, beta glucan, and gum arabic (see Whistler, R. L. (1993) *Industrial Gums: Polysaccharides and their derivatives* Eds. Whistler R L and BeMiller J. N. (Academic Press) pp 2).

Glucans are homopolysaccharides consisting only of glucose. However, since it is possible to link the glucose molecules in different stereochemical conformations, glucans are a diverse group of compounds with differing chemical, physical, and functional properties.

Chemical structures of polysaccharides are of prime importance in determining their properties. This can be appreciated by comparing the common properties of some common homoglucans. Thus, cellulose, a (1-4)-β-D-glucan, is water insoluble and highly crystalline compared to other polysaccharides. Amylose, a (1-4)-α-D-glucan, is sparingly soluble in water, crystallizes less well than cellulose, and can form rigid thermo-reversible gels. Dextran, a (1-6)-α-glucan, with a small degree of branching, is extremely water soluble and non-gel forming. (See Dea, I. C. M. in (1993) *Industrial Gums: Polysaccharides and their derivatives* Eds. Whistler R L and BeMiller J. N. (Academic Press) pp 21.).

Oat β(1-3) β(1-4) glucan is classified as a viscous gum, (see Wood, P J (1993) *Oat Bran* Ed P J Wood (American Association of Cereal Chemists, Inc. St. Paul, Minn.)). Cereal β(1-3) β(1-4) glucan are structural polysaccharides present in the cell wall of cereals as barley and oat, among others.

Oat β(1-3) β(1-4) glucan is recognised by the U.S. FDA as an agent that may aid the prevention of heart disease. In 1997, the FDA allowed oat products to make a health claim. It is important to note that no other beta glucan source, yeast, fungal, bacterial, or cereal are recognised as having these effects and makes an important point that it is the view of those skilled in the scientific and medical art that beta glucans are distinct and a structure function relationship exists.

Unmodified oat β(1-3) β(1-4) glucan forms highly viscous solutions in water at concentrations >0.75%. At concentrations >1.2% the solutions have the consistency of a thick hydrogel.

Glucans of significantly different molecular structure and with different physical and chemical properties compared to oat are found in yeast, fungi, and certain bacteria and genetically engineered bacteria. For example, gellan, polymeric (1-3)β-D-glucopyranosyl [β(1-3) glucan] produced in *Alcaligenes faecalis* is found in Curdlan J (Takeda Chemical Ind. Ltd.), β(1-4) α(1-6) glucopyranoside produced in *Aureobasidium pullulans* found in pullulan, and β(1-3) β(1-6) glucopyranoside found in yeast.

The molecular weight of the glucans varies with source. Table 1 shows the average molecular weight of typical gums.

TABLE 1

Typical Molecular Weight Range of Common Gums

| GUM | AVERAGE MOLECULAR WEIGHT |
|---|---|
| Oat β (1-3) β (1-4) glucan | 500,000-1,000,000 |
| Pullulan | 50,000-100,000 |
| Curdlan | ~500,000 |
| Methyl cellulose | 10,000-200,000 |
| Carrageenan | 4,500,000 |
| Xanthan | 15,000,000-50,000,000 |
| Sodium alginate | 10,000-18,000,000 |

Viscosity of a 1% solution of different polysaccharide gum solutions varies with origin and thus chemical nature. Table 2 shows the viscosity of 1% solutions of typical gums.

TABLE 2

Typical Viscosity Ranges of 1% Solutions of Common Gums, Measured at 25° C.

| GUMS | 1% SOLUTION VISCOSITY, cP |
|---|---|
| Oat β (1-3) β (1-4) glucan | 500-1000 |
| Pullulan | 2 |
| Gum arabic | 1-5 |
| Methyl cellulose | 200 |
| Tamarind gum | 100-200 |
| Guar gum | 2,000-3,000 |
| Locust bean gum | 2,000-3,000 |
| Xanthan | 2,000-3,000 |
| Sodium alginate | 200-700 |

High viscosity and solution pouring effects are undesirable in pouring films and in mixing formulations. Typically heat >50° C. is required to ensure fluidity in mixing and pouring. The high viscosity of native β(1-3) β(1-4) glucan teaches away from the use of these materials in the preparation of films.

The solubility properties of glucans differ according to their source. For example cereal β(1-3) β(1-4) glucans are normally soluble in aqueous solvents, whereas yeast (*Saccharomyces cerevisiae*) β(1-3) β(1-6) are insoluble in aqueous solvents. Soluble glucans are desirable. Yeast beta glucan has been solubilized by the addition of phosphate groups (see Williams et al. *Immunopharmacol.* 22: 139-156 (1991)0. Jamas et al. (U.S. Pat. No. 5,622,939) describes methods to extract soluble beta glucan from *Saccharomyces cerevisiae*. The method described is complex involving acid hydrolysis, base hydrolysis and the extensive use of centrifugation and ultrafiltration. No details are provided as to the stability of the solubilized yeast β(1-3) β(1-6) glucan.

Beta glucans affect the viscosity and hence the effectiveness of products derived from these sources. For example, beta glucans appear to influence digestion, assist in glucoregulation, and lower serum cholesterol. Cereal beta glucans are useful nutritional agents and have also been used as bulking agents in place of sucrose. Beta glucans have also been described as potent immune system stimulants and promote the healing of wounds (Yun et al. *Int. J. Parasitol.* (1997) 27:329-337; Estrada et al (1997)). The immune stimulatory activity of oat β(1-3) β(1-4) glucan is described by Estrada et at (1997, Microbiol. Immunol. 41:991-998). Differences in immune stimulation between β glucans from different sources are described.

Williams et al. (U.S. Pat. No. 5,676,967) describe a wound healing gauze for use in skin loss injuries and burns. The gauze described presents a combination oat β(1-3) β(1-4) glucan and collagen presented on a rigid support mesh. Self-supporting films of β(1-3) β(1-4) are not described.

Cereal β(1-3) β(1-4) glucan has also been used as a suspending solution for biocompatible particles for tissue injection (Lawin et al. U.S. Pat. No. 5,451,406).

Redmond (U.S. Pat. No. 6,284,886) describes methods and compositions of solutions of cereal β(1-3) β(1-4) glucan. The described compositions meet the restricted requirements of cosmetics industry which favours the use of beta glucan for its viscosity, shear strength, and moisture enhancing properties. No film or dry glucan preparations are described.

U.S. Pat. No. 6,323,338 discloses a method of isolating oat beta glucan as an enriched skin from an extract of oat bran. This reference does not disclose films comprising cereal beta glucan and a compound of interest, or a method of formulating these films.

There are a number of disclosures on the use of thin films made from a variety of polysaccharide material. These prior art references include for example: Japanese applications JP 5-236885 and JP 5-1198; U.S. Pat. Nos. 5,518,902; 5,411, 945; 4,851,394; 3,784,390; 4,623,394 and International PCT publications WO 99/17753; WO 98/26780; WO 98/20862; WO 98/26763 and WO 00/18365. These prior art thin film products can also include a variety of ingredients, for example antibacterial agents, flavouring agents, other polysaccharides and pharmaceutically active substances.

According to the present invention it has been found that the use of cereal β(1-3) β(1-4) glucan was advantageous in comparison with other gums since it formulates at lower percentages and surprisingly thin films are more easily formed with either no need for or reduced need for other gums in the finished formulation. Central to the present invention is the surprising ability of β(1-3) β(1-4) glucan to sequester hydrophobic materials and alcoholic extracts. This capacity lends itself to the remarkable oil carrying ratios of cereal β(1-3) β(1-4) glucan.

Edible films to date have been manufactured from lower molecular weight gums since the higher molecular weight gums typically have a high viscosity of solution which makes thin films difficult to obtain. The advantage of using oat beta glucan is that lower percentages of gel can be used in film formation. Further, with these lower percentages, the material may be poured cool which has a protective effect on associated materials such as volatile oils and pharmaceutical compounds which may be temperature sensitive.

SUMMARY OF THE INVENTION

In one aspect, the present invention provides a film comprising:
a β(1-3) β(1-4) glucan, and
an effective amount of one, or more than one compound of interest.

In another aspect, the present invention provides a method of producing a film or an article coated with a film comprising:
i) mixing an aqueous solution of a β(1-3) β(1-4) glucan with one, or more than one compound of interest to form a composition;
ii) drying the composition to form the film, or
iii) applying the composition to an article, and drying the applied composition to produce the article coated with the film.

In an embodiment of the method described above, after the glucan and the compound of interest are mixed they are left undisturbed for a period of time sufficient to form a homogeneous composition.

In a further embodiment of the method described above, the homogeneous composition is a homogeneous emulsion. In another embodiment, the homogeneous emulsion is formed in the absence of an emulsifying agent.

In another embodiment of the above-defined method, the aqueous solution is formed using a glucan having a purity in the range of from about 65% to about 100%, more preferably from about 75% to about 100%, most preferably from about 85% to about 100%.

In a further aspect, the present invention provides an article coated with one, or more than one layers of a film comprising:
a β(1-3) β(1-4) glucan, and
an effective amount of one, or more than one compound of interest.

In an embodiment of the above-defined article, each one of the one, or more than one layers comprises a separate compound of interest.

In a further embodiment of the above-described film, the amount of the β(1-3) β(1-4) glucan in the film is from about 5 wt % to about 50 wt %.

In an even further embodiment of the above-described film, the amount of the β(1-3) β(1-4) glucan in the film is from about 10 wt % to about 35 wt %.

In an even further embodiment of the above-described film, the amount of the β(1-3) β(1-4) glucan in the film is from about 15 wt % to about 25 wt %.

In another embodiment of the above-described film, the amount of the one, or more than one compound of interest is from about 0.001 wt % to about 50 wt %.

In a further embodiment of the above-described film, the amount of the one, or more than one compound of interest is from about 5 wt % to about 35 wt %.

In an even further embodiment of the above-described film, the amount of the one, or more than one compound of interest is from about 10 wt % to about 25 wt %.

In another embodiment, the above-defined film is a self-supporting film.

In another embodiment of the above-defined film, the glucan is derived from a cereal grain or a part of a cereal grain. Preferably, the cereal is selected from the group consisting of a cultivar of barley, a cultivar of oat, a cultivar of wheat, a cultivar of rye, a cultivar of sorghum, a cultivar of millet, a cultivar of corn, and a mixture thereof.

In another embodiment of the film defined above, the one, or more than one compound of interest is selected from the group consisting of a pharmaceutical agent, an antimicrobial agent, a flavouring agent, and a mixture thereof.

In a further embodiment of the film defined above, the one, or more than one compound of interest is a pharmaceutically active agent selected from the group consisting of a non-steroidal anti-inflammatory drug, an anti-tussive, a decongestant, an anti-histamine, an expectorant, an anti-diarrheal, an H2-antagonist, a nonselective central nervous system depressant, a nonselective central nervous system stimulant, an agent that selectively modifies central nervous system function, a drug for treating Parkinson's disease, a narcotic-analgesic, an analgesic-antipyretic, a psychopharmacological agent, and a mixture thereof.

In an even further embodiment of the film defined above, the one, or more than one compound of interest is an antimicrobial agent selected from the group consisting of triclosan, cetyl pyridinium chloride, sanguinarine, domiphen bromide, a quaternary ammonium salt, a zinc compound, a fluoride, alexidine, octonideine, EDTA, silver nitrate, thymol, methyl salicylate, eucalyptol, menthol, and a mixture thereof.

In further embodiments, the article described above is a pharmaceutical formulation in the form of a tablet or capsule; a stent; a tissue paper; or dental floss.

The present invention also relates to a pharmaceutical formulation comprising the film defined above. Preferably, the pharmaceutical formulation is a patch suitable for delivery of one, or more than one compound of interest.

BRIEF DESCRIPTION OF THE DRAWINGS

These and other features of the invention will become more apparent from the following description in which reference is made to the appended drawings wherein.

DESCRIPTION OF PREFERRED EMBODIMENT

Figure 1:
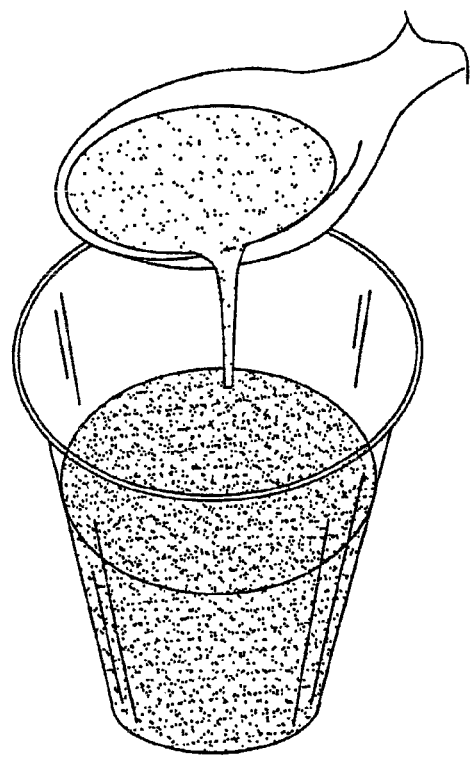
FIG. 1 shows a composition comprising oat $\beta(1\text{-}3)\ \beta(1\text{-}4)$ glucan, which is used to form the film of the present invention.

The practice of the present invention will employ, unless otherwise indicated, conventional methods of chemistry, cereal chemistry, and biochemistry, within the skill of the art. Such techniques are explained fully in the literature. See for example, *Industrial Gums: Polysaccharides and their derivatives* Eds. Whistler R L and BeMiller J. N. (Academic Press), *Oats: Chemistry and Technology* ed. Webster F H (American Association of Cereal Chemists, St. Paul, Minn.).

All publications, patents, and patent applications cited herein, whether supra or infra, are incorporated by reference in their entirety.

As used in this specification and the appended claims, the singular forms "a", "an" and "the" include plural references unless the content clearly indicates otherwise.

DEFINITIONS

In describing the present invention, the following terms will be employed, and are intended to be defined as indicated below.

By "cereal" is meant any of several grains such as, but not limited to, cultivars of barley, oat, wheat, rye, sorghum, millet, and corn.

By "glycan" is meant a polymer of monosaccharides linked together by glycosidic bonds.

By "glucan" is meant a homopolysaccharide consisting only of glucose.

By "cereal beta glucan" is meant a glucan with a $\beta(1\text{-}3)$-linked glucopyranosyl backbone, or a $\beta(1\text{-}4)$-linked glucopyranosyl backbone, or a mixed $\beta(1\text{-}3)\ \beta(1\text{-}4)$-linked glucopyranosyl backbone, which is derived from a cereal source.

By "$\beta(1\text{-}3)\ \beta(1\text{-}4)$ glucan" is meant a cereal $\beta$ glucan.

By "gum" is meant a plant or microbial polysaccharide or their derivatives that are dispersible in either cold or hot water to produce viscous mixtures or solutions. Gums may be classified by origin: exudate gums, seaweed gums, seed gums, starch and cellulose derivatives, and microbial gums.

By "compound of interest" is meant any pharmaceutical, medical, therapeutic, flavouring, fragrance or other functional materials mixed with the $\beta(1\text{-}3)\ \beta(1\text{-}4)$ glucan to produce a coatable composition or thin-film.

By "effective amount" is meant the amount of the one, or more than one compound of interest necessary to achieve a desired effect, such as a physiological effect, or a stimulatory effect.

By "sequester" is meant the incorporation, entrapment, or solubilization of hydrophilic compounds, or hydrophobic compounds, for example, small molecular weight hydrophobic compounds, such as essential oils, pharmaceutical, medical, and therapeutic agents.

In a preferred embodiment, the present invention provides a method of forming a film or an article coated with a film, the film comprising a $\beta(1\text{-}3)\ \beta(1\text{-}4)$ glucan and one, or more than one compound of interest, the method comprising:

i) mixing an aqueous solution comprising about 0.01 wt % to about 4.0 wt % of a $\beta(1\text{-}3)\ \beta(1\text{-}4)$ glucan with one, or more than one compound of interest to form a composition;

ii) drying the composition to form the film, or iii) applying the composition to an article, and drying the applied composition to produce the article coated with the film.

The method of the present invention can be used to provide films and coatings for use in cosmetic, confectionery, medical and pharmaceutical preparations.

The aqueous solution used in the method of the present application preferably contains the beta glucan in an amount of from about 0.01 wt % to about 1.2% wt %, more preferably about 0.1 wt % to about 1.1 wt %, most preferably about 0.5 wt % to about 1 wt %.

The beta glucan solution is preferably mixed with about 0.01 wt % to about 4.0 wt %, more preferably about 0.01 wt % to about 1.2% wt %, even more preferably about 0.1 wt % to about 1.1 wt %, most preferably about 0.5 wt % to about 1 wt % of one, or more than one compound of interest.

It is preferred that the beta glucan solution used in step (i) of the method of the present invention be prepared from a beta glucan having a purity of from about 65% to about 100%, more preferably from about 75% to about 100%, most preferably from about 85% to about 100%. It is particularly preferred that the beta glucan contain less than 35%, more preferably less than 25%, most preferably less than 15% of an impurity selected from the group consisting of a protein, a lipid, a carbohydrate, a particulate, and a mixture thereof.

If the compositions of the method of the present invention are to be used in the preparation of confectionery items, pharmaceutical compositions, or other related formulations, it is preferred that the beta glucan solution used in step (i) of the method be prepared from a beta glucan containing less than 20%, more preferably less 15%, even more preferably less than 10%, most preferably less than 5% of impurities, such as protein, lipid, carbohydrate, and particulate impurities.

Cereal beta glucans suitable for use in the method of the present invention are available in powdered form from several commercial suppliers, such as Sigma Chemical Co. (St. Louis, Mo.) and Ceapro Inc. (Edmonton, AB, Canada). Solutions of beta glucan can be prepared in the manner described in U.S. Pat. No. 6,284,886. If the films are for use in confectionery, pharmaceutical, or other related applications, then the preservatives used in the method described in U.S. Pat. No. 6,284,886 should be one that is approved for human consumption and pharmaceutical use, such as, but not limited to potassium sorbate, sorbic acid, benzalkonium chloride, and parabens.

In the method of the present invention, it is preferred that the composition comprising the beta glucan and the compound of interest, as illustrated in FIG. 1, be left undisturbed after the step of mixing (step i) for a period of time sufficient to allow the compound of interest to become completely sequestered by the glucan, so that a homogeneous composition comprising the glucan and the compound of interest is formed. In many cases, the amount of time required to obtain a homogeneous composition is from about 8 to about 16 hours. It is to be appreciated, however, that shorter or longer periods of time may be required, depending on the quantity and purity of the glucan used, as well as on the quantity and nature of the compound of interest. The homogeneous composition can be poured to different depths of a mold and dried or allowed to dry to a thin film. The dried films can then be cut into pieces of a desired size.

The composition can be allowed to air dry, can be dried with the application of heat, or can be dried under vacuum. The specific conditions that are used to dry the composition are dependent, however, on the nature of the compound of interest that has been sequestered by the glucan. For example, if the compound of interest is volatile, then the suspension can be allowed to air dry under ambient conditions, or can be dried using a low amount of heat.

Hydrophobic compounds, hydrophilic compounds and alcoholic extracts can all be sequestered by the beta glucan used in the method of the present invention. In particular, hydrophobic compounds having a molecular weight of <1500 MW, which are not appreciably soluble in aqueous solutions can be readily solubilized by the beta glucans used in the method of the present invention. Examples of such small molecular weight compounds include, without limitation, avenanthramides, flavonoids, saponins, vitamins, antibiotics, and other water insoluble drugs.

Generally, if the compound of interest is an oil or a hydrophobic material then the homogeneous composition is in the form of a homogeneous suspension or a homogeneous gel. Without wishing to be bound by theory, the formation of the homogeneous suspension or gel is caused by encapsulation of the oil or hydrophobic material by the beta glucan, and subsequent formation of hydrogen bonds between molecules of the oil or hydrophobic material and the beta glucan. Agitation of the gel generally converts it into a less viscous homogeneous suspension that can be poured to different depths of a mold. Generally, no additional emulsifying agent is required to prepare the homogeneous suspension of the present invention, as the beta glucan itself effectively acts as an emulsifying agent. If the compound of interest is a hydrophilic material, hydrogen bond formation can take place between the backbone of the beta glucan and the compound of interest, resulting in a homogeneous composition that can be in the form of a solution, or a viscous gel.

Other methods for forming the films of the present invention, such as the one described in U.S. Pat. No. 4,562,020, the disclosure of which is incorporated herein by reference, are known to those skilled in the art.

The films produced according to the method of the present application can be self-supporting independent structures, or can form one, or more than one layer on a support material, for example, a pharmaceutical formulation, or an edible material, such as, and without limitation to a confectionery item.

Figure 2:
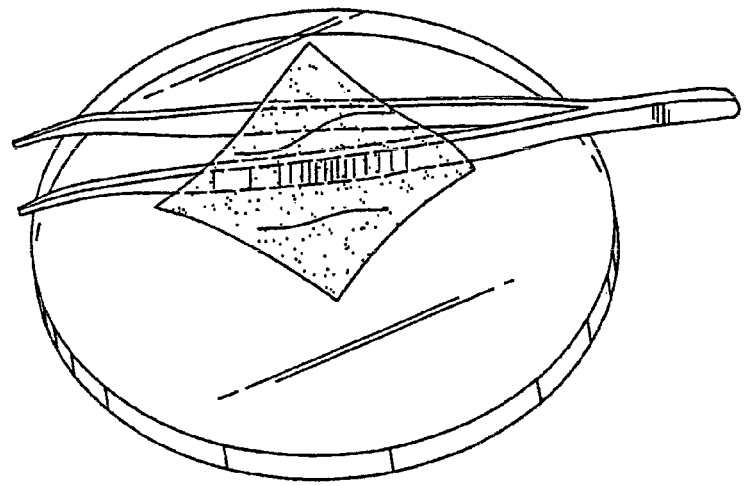
FIG. 2 shows an example of a film produced according to the present invention.

The films of the present invention can be prepared in a variety of thicknesses. The specific thickness of the film that is prepared according to the present invention will be dependent, however, on the particular application to which it is directed. For example, if the films of the present application are self-supporting, their thickness can range from about 1 µm to about 10 µm, more preferably from about 1 µm to about 4 µm. If the films of the present application are used as a coating on an article, then their thickness can range from about 0.001 µm to about 2 µm, more preferably from about 0.01 µm to about 0.1 µm. An example of a self-supporting film according to the present invention is illustrated in FIG. 2.

In an embodiment of the film of the present invention, the amount of the β(1-3) β(1-4) glucan in the film is from about 5 wt % to about 50 wt %. In a further embodiment, the film comprises from about 10 wt % to about 35 wt % β(1-3) β(1-4) glucan. In an even further embodiment, the film comprises from about 15 wt % to about 25 wt % β(1-3) β(1-4) glucan.

In another embodiment of the film of the present invention, the amount of the one, or more than one compound of interest in the film is from about 0.001 wt % to about 50 wt %. In a further embodiment, the amount of the one, or more than one compound of interest in the film is from about 5 wt % to about 35 wt %. In an even further embodiment, the amount of the one, or more than one compound of interest in the film is from about 10 wt % to about 25 wt %.

The composition formed in the method of the present invention can be used to coat an article, by applying the composition as an aerosol spray to the article, or by dipping the article in the composition. These types of application are particularly useful for coating non-easily wrapped or enrobed objects, or delicate or sensitive materials, especially those that are temperature or moisture sensitive. Aerosol application is also particularly useful in applying a thin film of coating to absorbent surfaces, particularly tissue for facial or toilet applications.

The composition formed in the method of the present invention can also be processed into a fiber. For example, fibers prepared from the compositions of the present invention, which contain an anti-microbial agent, can be used to form dental floss or surgical sutures. Alternatively, the compositions can be applied to conventional dental floss or surgical sutures, and allowed to dry to a film.

Cereal beta glucan is considered to be a mucilaginous gum with inherent slippery characteristics. The slip property of the cereal beta glucan component in the compositions of the present invention can be used to ease the insertion of stents or other medical devices coated with a film derived from these compositions.

By incorporating other ingredients in the compositions of the present invention, or by modifying the manner in which these compositions are dried, the films resulting from these compositions can demonstrate an adhesive property, which is useful in binding materials to the mouth, tongue, gums, skin, or a wound.

Film formulations can be modified to produce different physical properties. By adjusting the amounts and types of the constituents of the film, the film thickness and drying times, films can be produced that range from being pliable to brittle. For instance, the addition of powdered fructose to the compositions of the present invention can produce a hard film. Alternatively, unsweetened hard films can be produced by means of rapid drying using vacuum drying techniques.

Similarly, the release kinetics of a compound of interest contained within the films of the present invention can be adjusted by modifying the composition of the films of the present invention or by changing the degree to which they are dried. This property is of importance in a number of pharmaceutical or medical applications.

The films of the present invention are preferably readily dissolvable and can act as a vehicle for administering a pharmaceutically active agent through a mucous membrane or an open wound of a patient. The films of the present invention can also be used as an enteric coating on formulations that are in the form of a tablet or capsule. As an example, these films can contain flavouring agents that mask the taste of the active ingredient in the formulation or prevent the active ingredient from numbing the tongue or other surfaces of the oral cavity.

Tactile and sensory "popping" may be incorporated into films of the present invention to produce items for use in the confectionery industry. The popping characteristic can be introduced into these films by adding air into the compositions of the present invention after a thickening agent, such as carageenan, has been added, and, optionally by lengthening the drying time of these compositions. Aeration can be achieved by rapid whisking of the solution prior to pouring. Alternatively, air can be bubbled into the solution until the desired consistency is obtained.

The films of the present invention can also be used as a laminate or coating for an edible material. As an example, different coatings comprising different flavouring agents can be applied to an edible material, so that different flavours are released at different times when the laminated edible material is dissolved in the mouth. This property is of particular interest to the confectionery industry. Therefore, the films and coatings of the present invention can be of use in nutraceuticals. In addition, the films of the present invention can also be used as a source of dietary fibre.

The films of the present invention can not only be taken orally, but can also be used as a topical patch to deliver one, or more than one compound of interest, such as pharmaceutically active compounds. In another embodiment, the film of the present invention may form part of an existing patch that is suitable for delivering one, or more than one compound of interest.

In another aspect of the present invention, there is provided a sweetener composition comprising:
a β(1-3) β(1-4) glucan, and
an effective amount of a sweetener.

In a preferred embodiment of the above-defined sweetener composition, the sweetener is effective in producing a favourable stimulatory response in the absence of other sweeteners.

In a particularly preferred embodiment of the above-defined sweetener composition, the sweetener is Acesulfame-K.

The beta glucan content of the films of the present application can be determined using a number of methods, known to those skilled in the art. For example, beta glucan content can be assessed colorimetrically and/or by standard analytical techniques such as size exclusion chromatography and HPLC (see Wood et al. *Cereal Chem.* (1977) 54:524; Wood et al. *Cereal Chem.* (1991) 68:31-39; and Wood et al. *Cereal Chem.* (1991) 68:530-536). Beta glucans can also be analyzed enzymatically using commercially available kits, such as Megazyme (Ireland) employing the techniques of McCleary and Glennie-Holmes *J. Inst. Brew.* (1985) 91:285.

Viscosities can be measured with a rotational, shear-type viscometer such as the Brookfield Syncro-Lectric or the Haake Rotovisco. Methods of using the instrument are known to those skilled in the art. Routinely, measurements are made at four speeds of disc rotation at a constant temperature of 25° C.

The films and coatings compositions of this invention can contain colouring agents or colourings. The colouring agents are used in amounts effective to produce the desired color. The colouring agents useful in the present invention, include pigments such as titanium dioxide, which may be incorporated in amounts of up to about 5% wt, and preferably less than about 1% wt. Colourings can also include natural food colours and dyes suitable for food, drug and cosmetic applications. These colorants are known as FD&C dyes and lakes. The materials acceptable for the foregoing spectrum of use are preferably water-soluble, and include FD&C Blue No. 2, which is the disodium salt of 5,5-indigotindisulfonic acid. Similarly, the dye known as Green No. 3 comprises a triphenylmethane dye and is the monosodium salt of 4-[4-N-ethyl-p-sulfobenzylamino)diphenyl-methylene-1-[1-N-ethyl-N-p-sulfonium benzyl)-2,5-cyclo-hexadienimine]. A full recitation of all FD&C and D&C dyes and their corresponding chemical structures may be found in the Kirk-Other Encyclopaedia of Chemical Technology, Volume 5, pp 857-884, which text is accordingly incorporated herein by reference.

If produced for edible consumption the coating or thin film may contain flavouring. (Those for external use need not contain flavouring). The flavourings that can be used include those known to the skilled artisan, such as natural and artificial flavours. These flavourings may be chosen from synthetic flavour, oils and flavouring aromatics, and/or oils, oleo resins and extracts derived from plants, leaves, flowers, fruits and so forth, and combinations thereof. Representative flavouring oils include: spearmint oil, cinnamon oil, peppermint oil, clove oil, bay oil, thyme oil, cedar leaf oil, oil of nutmeg, oil of sage, and oil of bitter almonds. Also useful are artificial, natural or synthetic fruit flavours such as vanilla, chocolate, coffee, cocoa and citrus oil, including lemon, orange, grape. lime and grapefruit and fruit essence including apple, pear, peach, strawberry, raspberry, cherry, plum, pineapple, apricot, and so forth. These flavourings can be used individually or in a mixture. Commonly used flavours include mints, for example peppermint and/or spearmint, artificial vanilla, cinnamon derivatives, and various fruit flavours, whether employed individually or in combination. Flavourings such as aldehydes and esters including cinnamyl acetate, cinnamaldehyde, citral, diethylacetal, dihydrocarvyl acetate, eugenyl formate, p-methylanisole, and so forth may be used. Generally, any flavouring or food additive, such as those described in Chemicals Used in Food Processing, publication 1274 by the National Academy of Sciences, pp 63-258. Further examples of aldehydes include, but are not limited to acetaldehyde (apple); benzaldehyde (cherry, almond); cinnamic aldehydes (Cinnamon); citral i.e. (lemon, lime); neral i.e. beta citral (lemon, lime); decanal (orange, lemon); ethyl vanillin (vanilla, cream); heliotropine, i.e. piperonal (vanilla, cream); vanillin (vanilla, cream); alpha-amyl cinnamaldehyde (spicy fruity flavours); butyraldehyde (butter, cheese); valeraldehyde (butter, cheese); citronellal; decanal (citrus fruits); aldehyde C-8 (citrus fruits); aldehyde C-9 (citrus fruits), aldehyde C-12 (citrus fruits); 2-ethyl butyraldehyde (berries); hexanal i.e. trans-2 (berries); tolyl aldehyde (cherry, almond); veratraldehyde (vanilla); 2,6-dimethyl-5-heptenal, i.e. melonal (melon); 2-6-dimethyloctanal (green fruit); and 2-dodecenal (citrus, mandarin); cherry, grape; and mixtures thereof.

The amount of flavouring used is normally a matter of preference subject to such factors as flavour type, individual flavour, and strength desired. Thus, the amount may be varied in order to obtain the result desired in the final product. Such variations are within the capabilities of those skilled in the art without the need for undue experimentation. In general, amounts of about 0.1 to about 30% wt are usable with amounts of about 2 to about 25% wt being preferred and amounts from about 8 to about 12% wt are more preferred.

Addition of sweeteners to the coating or film is optional if the product is for edible consumption. In general, an amount of auxiliary sweetener is utilized to provide the level of sweetness desired in a particular composition, and the amount will vary with the sweetener selected. This amount will normally be 0.01% to about 10% by weight of the composition when using an easily extractable sweetener. The selection and amount of sweetener used is within the capabilities of those skilled in the art without the need for undue experimentation. Other considerations will include the interaction with flavouring.

Sweeteners will be selected either individually or as combinations of sweeteners selected from the following groups:
1. Water-soluble sweeteners are well known in the art. These include, but are not limited to, monosaccharides, disaccharides, and polysaccharides such as xylose, ribose, glucose, dextrose, mannose, galactose, fructose (levulose), sucrose (table sugar), maltose, invert sugar (glucose and fructose) partially hydrolysed starch, corn syrup solids, dihydrochalcones, monellin, steviosides, and glycyrrhizin.
2. Artificial sweeteners such as soluble saccharin salts, cyclamate salts, the sodium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (acesulfame-K), the free acid form of saccharin, and the like.
3. Dipeptide based sweeteners, such as L-aspartic acid derived sweeteners, such as L-aspartyl-L-phenylalanine methyl ester (aspartame) and materials describe in U.S. Pat. No. 3,492,131. L-alpha-aspartyl-N-(2,2,4,4-tetramethyl-3-thietanyl)-D-alaninamide hydrate, methyl esters of L-aspartyl-L-phenylglycerin and L-aspartyl-L-2,5, dihydrophenyl-glycine, L-aspartyl-2,5-dihydro-L-phenylalanine, L-aspartyl-L-(1-cyclohexyen)-alanine, and the like.
4. Water soluble sweeteners derived from naturally occurring water-soluble sweeteners, such as a chlorinated derivative of sucrose (Sucralose).
5. Protein based sweeteners such as thaumatoccous danielli (Thaumatin I and II).

The compositions of the present invention can also include surfactants. If surfactants are present, they can include mono and diglycerides of fatty acids and polyoxyethylene sorbitol esters, for example, Atmos 300 and Polysorbate 80. The amount of surfactant added is typically in the range of about 0.1 to about 15% by wt and preferably about 0.4 to about 5% by wt of the film/coating. Other surfactants will be known to those skilled in the art and may readily be employed without undue experimentation.

The compositions of the present invention can also include thickening agents. If thickening agents are present, they can include methylcellulose, hydroxypropyl carboxy methylcellulose (Methocel), or carboxy methylcellulose (CMC), and the like, are typically used in amounts ranging from about 0 to about 5% by wt., preferably about 0.01 to about 0.7% by wt of the film/coating.

Saliva stimulating agents can also be added to the oral care films according to the present invention. Useful saliva stimulating agents are those disclosed in U.S. Pat. No. 4,820,506, which is incorporated by reference herein in its entirety. Saliva stimulating agents include food acids such as citric, lactic, malic, succinic, ascorbic, adipic, fumaric, and tartaric acids. Preferred food acids are citric, malic, and ascorbic acids. The amount of saliva stimulating agents in the film is from about 0.01 to about 12% by wt, preferably about 1 to about 10% by wt, even more preferably about 2.5% by wt. to about 6% wt.

For oral preparations it may be desirable to provide a cooling sensation on dissolving the film. Preferred cooling agents include mono-menthyl succinate, in amounts ranging from about 0.001 to about 2.0 wt %, preferably about 0.2 to about 0.4 wt %. A mono-menthyl succinate containing cooling agent is available from Mane, Inc. Other suitable cooling agents include WS3, WS23, Ultracool II, and the like.

Preferred antimicrobial agents, include for example antimicrobial agents, such as triclosan, cetyl pyridium chloride, sanguinarine, domiphen bromide, quaternary ammonium salts, zinc compounds, fluorides, alexidine, octonidine, EDTA, silver nitrate, thymol, methyl salicylate, eucalyptol, menthol and the like.

The expression "pharmaceutically active agents" as used herein is intended to encompass agents other than foods, which promote a structural and/or functional change in and/or on bodies to which they have been administered. These agents are not particularly limited; however, they should be physiologically acceptable and compatible with the film. Suitable pharmaceutically active agents include, but are not limited to:

Non-steroidal anti-inflammatory drugs, such as aspirin, diflunisal, fenoprofen calcium, naproxen, acetaminophen, ibuprofen, ketoprofen, tolmetin sodium, indomethacin, and the like, Anti-tussives, such as benzonatate, caramiphen edisylate, menthol, dextromethorphan hydrobromide, chlophedianol hydrochloride, and the like, Decongestants, such as pseudoephedrine hydrochloride, phenylepherine, phenylpropanolamine, pseudoephedrine sulfate, and the like, Anti-histamines, such as brompheniramine maleate, chlorpheniramine maleate, carbinoxamine maleate, clemastine fumarate, dexchlorpheniramine maleate, diphenhydramine hydrochloride, diphenylpyraline hydrochloride, azatadine meleate, diphenhydramine citrate. doxylamine succinate, promethazine hydrochloride, pyrilamine maleate, tripelennamine citrate, triprolidine hydrochloride, acrivastine. loratadine, brompheniramine. dexbrompheniramine, and the like, Expectorants, such as guaifenesin, ipecac, potassium iodide, terpin hydrate, and the like, Anti-diarrheals, such a loperamide, and the like, H2-antagonists, such as famotidine, ranitidine, avenanthramide, tranilast, and the like; and proton pump inhibitors, such as omeprazole, lansoprazole, and the like, General nonselective CNS depressants, such as aliphatic alcohols, barbiturates and the like, General non-selective CNS stimulants such as caffeine, nicotine, strychnine, picrotoxin, pentylenetetrazol and the like, Drugs that selectively modify CNS function such as phenyhydantoin, phenobarbital, primidone, carbamazepine, ethosuximide, methsuximide, phensuximide, trimethadione, diazepam, benzodiazepines, phenacemide, pheneturide, acetazolamide, sulthiame, bromide, and the like, Antiparkinsonism drugs such as levodopa, amantadine and the like, Narcotic-analgesics such as morphine, heroin, hydromorphone, metopon, oxymorphone, levorphanol, codeine, hydrocodone, xycodone, nalorphine, naloxone, naltrexone and the like, Analgesic-antipyretics such as salycilates, phenylbutazone, indomethacin, phenacetin and the like, and Psychopharmacological drugs such as chlorpromazine, methotrimeprazine, haloperidol, clozapine, reserpine, imipramine, tranylcypromhe, phenelzine, lithium and the like.

The amount of medicament that can be used in the rapidly dissolving films, according to the present invention, is dependent upon the dose needed to provide an effective amount of the medicament. The doses to be administered will be known to those skilled in the art and may readily be employed without undue experimentation.

Cold therapeutic minerals, for example zinc, in the form of soluble salts i.e. zinc citrate; or zinc gluconate may be readily incorporated into the aqueous phase of the film/coating in concentrations known to those skilled in the art and may readily be employed without undue experimentation.

Thus, formulations of the present invention containing an appropriate pharmaceutical or medical agent have wide reaching applications.

The following examples are provided to exemplify the present invention. Variations and alterations will be readily apparent to those skilled in the art.

Materials

A 1 wt % aqueous solution of oat beta glucan having a purity of >85% was used in the following examples. This solution was either purchased directly from Ceapro Inc. (Edmonton, AB, Canada), or prepared from an oat beta glucan powder (>85% purity) also obtained from Ceapro Inc. Solutions were prepared from the beta glucan powder in the manner described in U.S. Pat. No. 6,284,886, using only preservatives approved for human consumption and pharmaceutical use, including but not limited to potassium sorbate, sorbic acid, benzalkonium chloride, and parabens.

EXAMPLE 1

Production of Pliable β(1-3) β(1-4) Glucan Thin Film Strips with Rapid Dissolving Action Phase A was prepared as follows:
1. Heat 10 g purified water (or equivalent) to 90° C.
2. Weigh out 0.4 g of Methocel, and wet with 10 g hot water, and disperse well
3. Immediately add 100 g 1% liquid Beta Glucan (Ceapro)
4. Add colouring as needed
5. Add 4 g powdered or granular Fructose
6. Add 1 g of Sucralose
7. Mix well and stir intermittently for 20 minutes.

Phase B was prepared as follows:
To 1 g of 95% Ethanol add 0.4 g of Atmos 300
Add 0.8 g of essential oil flavouring or equivalent and mix well.

Phases A and B are then thoroughly mixed or emulsified and poured to form thin films. The films were allowed to air dry or alternatively were allowed to dry under streams of warm air. The films were dried to a moisture content in the range 6-8% (w/w). The resulting water activity (Aw) ranged from 0.150-0.250.

The dry films were cut into strips and removed from the mould. The composition of rapid dissolving films are shown below in Table 3.

TABLE 3

COMPOSITION OF RAPID DISSOLVING FILMS

| Ingredient | Function | Name | Wt (g) | wt % | Film % |
|---|---|---|---|---|---|
| TF forming agent | water soluble polymer | 1% beta glucan | 1 | 0.93 | 16.7 |
|  |  | 0.4% potassium sorbate | 0.4 | 0.37 | 6.7 |
| Thickening Agent | increase viscosity | Methocel (Hydroxyproply CMC) | 0.4 | 0.37 | 6.7 |
| Colouring |  | FD&C Blue No. 2, Green No. 3 | 0.01 | 0.01 |  |
| Sweeteners |  | Fructose | 4 | 3.72 | 66.7 |
|  |  | Sucralose | 1 | 0.93 | 16.7 |
| Solubilizer |  | 95% Ethanol | 1 | 0.93 |  |
| Surfactant |  | Atmos 300 | 0.4 | 0.37 | 6.7 |
| Flavouring | taste Antibacterial agent | Spearmint Oil | 0.8 | 0.74 | 11.4 |
| Balance |  | Reverse Osmosis water | 98.6 | 91.63 |  |
| Total |  |  | 107.61 | 100.00 | 131.6 |

EXAMPLE 2

Production of β(1-3)β(1-4) Glucan Films with "Popping" Sensation on Dissolving

Phase A was prepared as follows:
Weigh out 100 g CEAPRO 1% liquid Beta Glucan (Ceapro)
Add colouring as needed
Add 10 g powdered or granular fructose
Add carrageenan gum and dispense well
Mix well and stir intermittently for 10 minutes.

Phase B was prepared as follows:
To 1 g of 95% Ethanol add 0.4 g of Atmos 300
Add 0.8 g of essential oil flavouring or equivalent and mix well.

Phases A and B were then combined by adding Phase B to Phase A to form Phase C. Phase C was heated to ~50-C for 3 minutes. Phase C was then poured into films while warm.

The films were allowed to air dry at 38° C. for 10-16 hours in a forced air dryer or equivalent. The dry films to size and removed from moulds.

EXAMPLE 3

Production of Production of β(1-3)β(1-4) Glucan Film Coatings by Spray Application The film compositions were mixed as described in the previous examples.

The mixed material was applied to materials using a standard aerosol device, providing an immediate coating on the product.

Using this method, thin coating films applied are fast drying.

EXAMPLE 4

Production of β(1-3)β(1-4) Glucan Thin Films Containing Oat Extracts

Thin films were prepared from oat extract with natural anti-histaminic and anti-oxidant activity.

Phase A was prepared as follows:
Heat 10 g purified water (or equivalent) to 90° C.
Weigh out 0.4 g of Methocel, and wet with 10 g hot water, and disperse well
Immediately add 100 g 1% liquid Beta Glucan (Ceapro)
Add colouring as needed
Add 4 g powdered or granular Fructose
Add 1 g of Sucralose
Mix well and stir intermittently for 20 minutes.
Phase B was as follows:
An ethanolic extract of oats was Colloidal Oat Extract, (Ceapro Inc. Edmonton, AB, Canada) manufactured according to the method described in PCT/EP00/04046 (WO 00/67626).
Phase B was added to Phase A to produce a mixture containing 15 ppm of avenanthramide.
Phases A and B are then thoroughly mixed or emulsified and poured to form thin films. The films were allowed to air dry or alternatively were allowed to dry under streams of warm air.

EXAMPLE 5

Production of a β(1-3)β(1-4) Glucan Film Containing an Antimicrobial Agent

Phase A was prepared as follows:
Weigh out 50 g CEAPRO 1% liquid beta glucan (Ceapro)
Add 50 mg of the sweetener Sunett® (Nutrinova Inc.; chemical name: Acesulfame K);
Add colouring as needed;
Add 20 mg potassium phosphate monobasic (Sigma) previously dissolved in 1 g DI/RO water;
Add 70 mg cetyl pyridinium chloride (CPC) USP (Sigma) previously dissolved in 5 g DI/RO water.
Phase B was prepared as follows:
To 1.5 g of essential oil flavouring or equivalent, add 0.40 g of ATMOS 300 and mix well.
Phase B was added to Phase A, homogenized for 15 seconds and allowed to set overnight.
The mixture was shaken lightly to liquefy the emulsion, and poured to form thin films. The films were allowed to dry under streams of warm air at 45° C. for six hours.
A typical film of 3×2 cm contains approximately 0.7-1.0 mg CPC.

EXAMPLE 6

Production of a β(1-3)β(1-4) Glucan Film Containing Vitamin E

Phase A was prepared as follows:
Weigh out 50 g CEAPRO 1% liquid beta glucan (Ceapro);
Add 50 mg of the sweetener Sunett® (Nutrinova; chemical name: Acesulfame K);
Add colouring as needed;
Add 20 mg potassium phosphate monobasic (Sigma) previously dissolved in 1 g DI/RO water;
Add 458 mg alpha-tocopherol succinate (Sigma).
Phase B was prepared as follows:
To 1.5 g of essential oil flavouring or equivalent, add 0.40 g of ATMOS 300 and mix well.
Phase B was added to Phase A, homogenized for 15 seconds and allowed to set overnight.
The mixture was shaken lightly to liquefy the emulsion, and poured to form thin films. The films were allowed to dry under streams of warm air at 45° C. for six hours. A typical film of 3×2 cm contains approximately 1.5 mg Vitamin E (equivalent to 3.3 IU or 1/10 the recommended daily allowance).

Alternatively, 458 mg alpha-tocopherol USP (Roche) may used instead of alpha-tocopherol succinate. This would be added to Phase B prior to mixing with Phase A.

EXAMPLE 7

Coating of Dental Floss with a β(1-3)β(1-4) Glucan Film Containing An Antimicrobial Agent Unwaxed Dental Floss (Oral-B Ultrafloss™), in the form of a ribbon, filament or braided filament, was sprayed or alternatively dipped in the antimicrobial composition prepared according to Example 5. Excess solution was removed, for example, by squeezing the coated floss between rollers, and the floss allowed to dry in warm air at 60° C. for ten to fifteen minutes.

EXAMPLE 8

Enteric Coating of Acetyl Salicylic Acid (ASA) with a Spray Dried β(1-3)β(1-4) Glucan Flavoured Film The film compositions were mixed as described in the previous examples.

ASA tablets were evening sprayed with a light misting with the above beta glucan formulation.

The tablets were then hot air dried for 3 minutes at 75° C.

The present invention has been described with regard to preferred embodiments. However, it will be obvious to persons skilled in the art that a number of variations and modifications can be made without departing from the scope of the invention as described in the following claims.

The embodiments of the invention in which an exclusive property or privilege is claimed are defined as follows:

1. A composition comprising:
   a β(1→3) β(1→4) glucan, and
   one or more than one compound of interest selected from the group consisting of a pharmaceutically active agent, an antimicrobial agent, a flavouring agent and a mixture thereof,
   wherein the β(1→3)β(1→4) glucan is in the form of a fibre selected from the group consisting of a dental floss or a surgical suture.

2. The composition according to claim 1, wherein the fibre is dental floss.

3. The composition according to claim 1, wherein the fibre is a surgical suture.

* * * * *

UNITED STATES PATENT AND TRADEMARK OFFICE
CERTIFICATE OF CORRECTION

Page 1 of 1

PATENT NO. : 8,632,798 B2
APPLICATION NO. : 12/716588
DATED : January 21, 2014
INVENTOR(S) : Mark J. Redmond et al.

It is certified that error appears in the above-identified patent and that said Letters Patent is hereby corrected as shown below:

In the Specification

Col. 3, line 18: "at" should be -- al. --

Col. 12, line 50, "rate." should be -- rate, --

Col. 12, line 52, "acrivastine." should be -- acrivastine, --

Col. 12, line 53, "brompheniramine." should be -- brompheniramine, --

Col. 12, lines 65-66, "phenyhydantoin," should be -- phenylhydantoin, --

Col. 13, line 15, "tranylcypromhe," should be -- tranylcypromine, --

Col. 16, lines 15-16, "may used" should be -- may be used --

Signed and Sealed this
Seventh Day of April, 2015

Michelle K. Lee
*Director of the United States Patent and Trademark Office*